(12) United States Patent
Dahlhaus et al.

(10) Patent No.: US 6,441,234 B1
(45) Date of Patent: Aug. 27, 2002

(54) PRODUCTION OF FORMAMIDE USING SODIUM DIFORMYLAMIDE

(75) Inventors: Jürgen Dahlhaus, Limburgerhof; Jörn Karl, Mannheim; Michael Schulz, Ludwigshafen; Anne Wenzel, Graben-Neudorf; Wolfgang Harder, Weinheim; Arthur Höhn, Kirchheim, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/889,405

(22) PCT Filed: Dec. 23, 1999

(86) PCT No.: PCT/EP99/10384

§ 371 (c)(1),
(2), (4) Date: Jul. 17, 2001

(87) PCT Pub. No.: WO00/41995

PCT Pub. Date: Jul. 20, 2000

(30) Foreign Application Priority Data

Jan. 18, 1999 (DE) .......................................... 199 01 744

(51) Int. Cl.[7] .............................................. C07C 233/03
(52) U.S. Cl. ....................... 564/132; 564/123; 564/215; 564/216
(58) Field of Search ................................. 564/132, 123, 564/215, 216

(56) References Cited

U.S. PATENT DOCUMENTS

| 3,781,352 A | 12/1973 | Hawthorne |
| 4,098,820 A | 7/1978 | Couteau |
| 5,919,979 A | 7/1999 | Mitchell |

FOREIGN PATENT DOCUMENTS

| DE | 27 10 725 | 9/1977 |
| DE | 44 33 507 | 3/1995 |
| GB | 2 216 035 | 10/1989 |

OTHER PUBLICATIONS

Ullman's Ency of Ind.Chem. vol. A12 (1989, XP–002137322.

*Primary Examiner*—Sreeni Padmanabhan
(74) *Attorney, Agent, or Firm*—Keil & Weinkauf

(57) ABSTRACT

In the process for preparing formamide by reaction of ammonia and carbon monoxide in the presence of at least one catalyst, sodium diformylamide is used as catalyst. If sodium methoxide is used as further active component, sodium diformylamide can be formed from this. In this process, sodium diformylamide is a particularly active and stable catalyst which can be recycled.

11 Claims, 1 Drawing Sheet

PRODUCTION OF FORMAMIDE USING SODIUM DIFORMYLAMIDE

This application is a 371 of PCT/EP99/10384 filed Dec. 23, 1999, now WO 00/41995 published Jul. 20, 2000.

The present invention relates to a process for preparing formamide by reaction of ammonia and carbon monoxide.

Formamide ($NH_2CHO$) is an excellent nonaqueous solvent for many inorganic salts (e.g. chlorides of copper, lead, zinc, tin, cobalt, iron, aluminum and nickel; acetates of the alkali metals, etc.). It also dissolves, for example, gelatin, glucose, starch, polyvinyl alcohol and cellulose acetates. Owing to its bifunctionality (carbonyl and amide group), formamide is capable of undergoing numerous reactions in organic chemistry. It reacts with formaldehyde to form a hydroxymethyl derivative, is converted catalytically into acrylonitrile, decomposes at >200° C. into carbon monoxide, ammonia, hydrocyanic acid and water and hydrolyzes very slowly at room temperature, more rapidly at higher temperatures and in the presence of acids or bases.

Formamide is used, in particular, as solvent for producing vitamins, formic acid and hydrocyanic acid, for softening size and paper, as swelling agent in permanent wave fluid, etc.

Formamide is generally prepared from the raw materials carbon monoxide and ammonia. This involves catalytic reactions in which suitable catalysts are, in particular, metal catalysts such as ruthenium catalysts or alkoxides such as sodium methoxide or sodium ethoxide. Processes employed to date which make use of alkoxides as catalyst are two-stage processes in which carbon monoxide and methanol are reacted to give methyl formate in a first stage. The catalyst, usually sodium methoxide, decomposes under the reaction conditions to form sodium formate. This salt generally deposits in the apparatus used which then has to be flushed regularly to free it of salt, which has the disadvantage of loss of production time. In a second stage, the methyl formate reacts with ammonia in the absence of catalysts to produce formamide. Production processes for formamide are usually continuous processes.

In the following we will concern ourselves with a single-stage production process. In GB-A-2 216 035, the reaction conditions are selected so that the solvent remains in the reactor. Use is made of high-boiling solvents (having a boiling point higher than that of formamide) so that formamide can be distilled directly from the reaction mixture and the solvent does not have to be worked up.

Apart from being able to separate off the formamide product easily and being able to regenerate the solvent as simply as possible, there is the additional aim of being able to reuse the catalyst. The catalyst, namely an alkoxide, i.e. a homogeneous catalyst, is normally removed from the reactor in the work-up and is decomposed, for example, by quenching. DE-C-44 33 507 describes the synthesis of formamide using alkali metal ethylene glycolates as catalyst and ethylene glycols as solvent. Owing to the high boiling point of ethylene glycol, which simultaneously functions as a reactant, formamide can readily be distilled from the reaction mixture. In addition, it is possible to recover the catalyst, namely the alkali metal ethylene glycolate, and to reuse it subsequently. However, the high boiling point of the solvent has the disadvantage that it promotes the decomposition of the catalyst.

In the recovery of these alkoxides, it needs to be borne in mind that losses of catalyst occur. This is because, in particular, alkoxides are generally readily hydrolyzed by water. In addition, other secondary reactions take place.

Alkoxides can, for example, decompose, which is promoted by relatively high temperatures. A substantial disadvantage of this process is, as mentioned above, the quite low stability of the catalyst used.

It is an object of the present invention to provide a process in which the direct synthesis of formamide from carbon monoxide and ammonia proceeds in such a way that the product can easily be separated from the reaction mixture and, in addition, the catalyst is recovered and reused. It should use a catalyst having a high catalytic activity and a high stability (in particular thermal and chemical stability). It should be possible to recycle the catalyst without problems. During the reaction and work-up, only small losses of the catalyst should occur. In addition, unreacted starting materials as well as solvents should be able to be recovered and be available for reuse in the reaction. A significant aspect is that carbon monoxide should be able to be used not only as a pure substance but also together with hydrogen or other inert gases. Hydrogen therefore has to be inert under the process conditions chosen.

We have found that this object is achieved by a process for preparing formamide by reaction of ammonia and carbon monoxide in the presence of at least one catalyst if sodium diformylamide is used as catalyst.

In a preferred embodiment, the reaction is carried out in the presence of at least one alcohol, preferably in the presence of methanol.

In a further embodiment, the process for preparing formamide by reaction of ammonia and carbon monoxide takes place in the presence of the catalyst sodium diformylamide and a further active component in a reactor to form a formamide-containing reaction mixture and the reaction mixture is subsequently worked up in an apparatus. Here, sodium diformylamide is formed from the active components during the reaction in the reactor and/or during the work-up in the apparatus and sodium diformylamide and/or a mixture containing sodium diformylamide is separated off in the apparatus and fed into the reactor.

In a particularly preferred embodiment, the active component is an alkoxide, preferably sodium methoxide. For the purposes of the present invention, the terms sodium methoxide and sodium diformylamide refer not only to the sodium salts themselves but also to all comparable salts which can form alkoxide or diformylamide—any cation can be chosen in principle. Preferred alkoxides and diformylamides are the corresponding alkali metal and alkaline earth metal salts (for example potassium methoxide or potassium ethoxide). The reaction of ammonia and carbon monoxide proceeds according to the following simplified reaction scheme:

$$NH_3 \;+\; CO \;\xrightarrow{[NaN(CHO)2]}\; NH_2CHO$$

In the novel process for preparing formamide, the reaction is usually carried out at from 50 to 200° C., preferably from 100 to 110° C. In general, the reaction takes place at pressures of from 10 to 200 bar. The abovementioned temperatures and pressures are in the reactor in which the reaction takes place.

In the process of the present invention, carbon monoxide can be supplied in the form of a mixture comprising carbon monoxide and hydrogen, preferably synthesis gas. The mixture comprising carbon monoxide and hydrogen is generally then fed into the reactor. It is thus possible to choose to use either pure carbon monoxide or a gas comprising carbon monoxide. Synthesis gas having a high proportion of hydrogen (>50%) can also be used. This is made possible by the fact that hydrogen is inert under the reaction conditions preferred according to the present invention (in particular the catalyst, the temperature, the pressure and the solvent). Synthesis gas is generally significantly cheaper than pure carbon monoxide, so that its use gives a cost advantage.

In the process of the present invention, the reaction is preferably carried out in the presence of at least one alcohol, preferably in the presence of methanol.

A significant step on the way to discovering the process of the present invention was possibly that it was found that sodium methoxide is converted into sodium diformylamide under the above-described conditions (solvent, temperature, pressure)—sodium diformylamide is thus a downstream product of sodium methoxide. Sodium diformylamide is a significantly more stable catalyst than sodium methoxide. For example, it reacts with water significantly more slowly than does sodium methoxide (is thus less susceptible to hydrolysis).

A further important advantage of sodium diformylamide is that it, in contrast to alkoxides, forms no insoluble salts in the reaction mixture under the prevailing reaction conditions, so that the abovementioned blockage problems do not occur when using sodium diformylamide.

The particular stability of the sodium diformylamide catalyst allows it to be recovered and to be reused in the reaction.

The reaction mixture formed in the reactor is generally passed directly to work-up in the apparatus. In this apparatus, in particular, materials separation by distillation takes place. In addition, a large part of the sodium methoxide transferred to the apparatus (assuming that sodium methoxide is used) is converted into sodium diformylamide in the apparatus. In general, the reaction mixture from the reactor is first separated into liquid and gaseous constituents in a separator and the liquid product is freed of methanol (if methanol is used as alcohol) in a first column and the methanol (if used) is returned to the reactor. Subsequently, after passage through a heat exchanger, the catalyst is usually separated from the formamide product in a second column. However, the catalyst is generally not isolated as a pure substance but is separated off in the form of a mixture comprising sodium diformylamide and formamide, preferably at least 60% by weight of formamide.

The mixture separated off is generally an about 20% strength by weight solution of the catalyst in formamide. While part of this solution is generally bled off in order to prevent accumulation of decomposition products, the other part of this solution is preferably returned to the reactor. Thus, in this continuous production process for formamide, the catalyst is recovered and recycled.

Sodium methoxide is the precursor of the actual sodium diformylamide catalyst; sodium diformylamide is possibly a reaction product of sodium methoxide and formamide. The sum of the concentrations of sodium methoxide and sodium diformylamide in the reactor is usually from 0.05 to 1.0 mol/l, preferably from 0.2 to 0.25 mol/l. Losses of sodium methoxide and/or sodium diformylamide are generally compensated for by metering further amounts of sodium methoxide into the reactor. Preferably, sodium methoxide in the form of a 30% strength by weight methanolic solution is added to the reaction mixture. In principle, it is also possible to meter additional sodium diformylamide into the reactor.

Unreacted carbon monoxide and/or unreacted ammonia and/or alcohol are generally taken from the apparatus and recirculated to the reactor.

The alcohol used is frequently methanol. In this case, the molar ratio of ammonia to carbon monoxide to methanol is generally 1.0:1.0–1.5:0.5–1.5. The ratio 1.0:1.25:1.0 has been found to be particularly useful. The pressure in the reactor is, as described above, preferably from 10 to 200 bar. When using pure carbon monoxide, a pressure of 40 bar is preferred and when using a gas comprising carbon monoxide, for example synthesis gas, a pressure of 120 bar is preferred.

The invention is illustrated by the examples below.

BRIEF DESCRIPTION OF THE DRAWING

In the accompanying drawing, FIG. 1 schematically shows the principle of a preferred embodiment of a plant in which the process of the present invention can be carried out.

EXAMPLE 1

Figure 1:
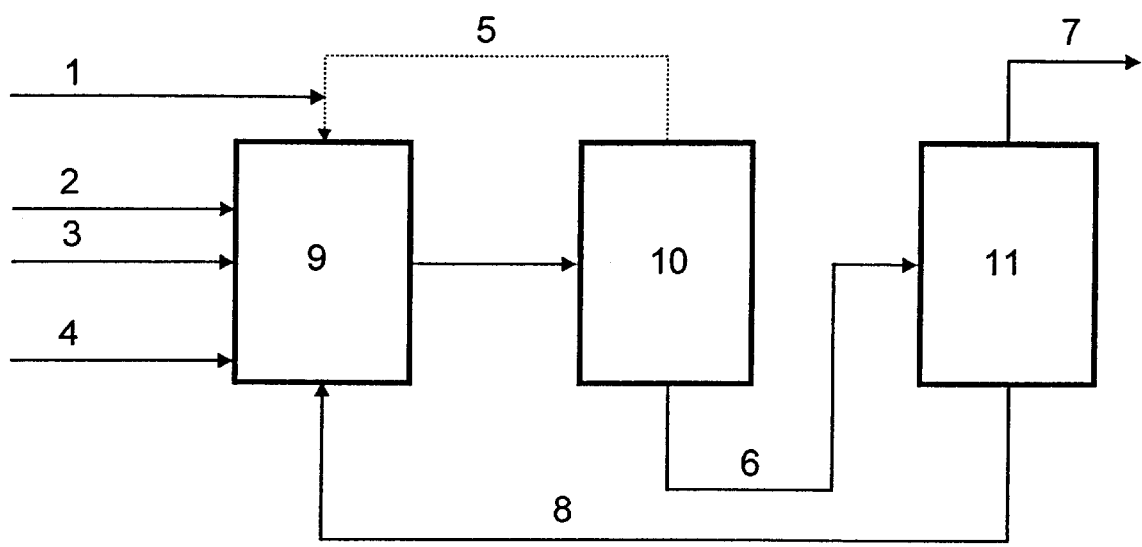

The reactor 9 of the plant comprises a stirring autoclave fitted with a disk stirrer and baffles. The reactor volume was 230 ml. Liquid ammonia as starting material was meter ed in to the reactor via the feed line 2. Carbon monoxide was metered in in gaseous form via the line 3. Methanol and the catalyst solution (30% m/m sodium methoxide in methanol) were pumped into the reactor via line 4. The reaction mixture was discharged from the reactor into the apparatus which essentially comprises two distillation stages 10, 11. The reaction mixture was first depressurized to about 5 bar, resulting in the major part of the unreacted carbon monoxide being given off. The subsequent work-up was carried out in two stages: in the first stage, methanol was removed by distillation at atmospheric pressure and was subsequently returned to the reactor via line 5. In the second stage 11, the major part of the formamide formed was distilled off via the top under reduced pressure (about 23 mbar) and taken off via line 7. The remaining formamide from the bottom of the second vaporizer was taken off together with the catalyst dissolved therein and 10% of the bottoms were bled off from the reactor. The resulting losses were compensated for by introduction of fresh 30% strength by weight sodium methoxide in methanol. The plant was operated at 40 bar, 100° C. and a ratio of the starting materials ammonia to carbon monoxide to methanol of 1.00:1.25:1.00. The average formamide yield based on ammonia was 96% and the space-time yield was 400 g of formamide/l/h.

EXAMPLE 2

The procedure of Example 1 was repeated using synthesis gas (ratio of carbon monoxide to hydrogen=45:55) at 120 bar and 100° C. and a ratio of the starting materials ammonia to carbon monoxide to methanol of 1.00:1.25:1.00. The average formamide yield was 96% based on ammonia at a space-time yield of 400 g of formamide/l/h.

EXAMPLE 3

The procedure of Example 1 was repeated using sodium diformylamide in methanol in place of sodium methoxide. The reaction was carried out at 40 bar and 100° C., and the amount of sodium diformylamide was 3–4% by weight, based on formamide. The average formamide yield was 92% at a space-time yield of 370 g of formamide/l/h.

We claim:

1. A process for preparing formamide by reaction of ammonia and carbon monoxide in the presence of at least one catalyst and at least one alcohol in a reactor, wherein the formamide containing reaction mixture is fed out of the reactor into a separate apparatus and worked-up there and the catalyst, being sodium methoxide and/or sodium diformylamide, is separated off in the apparatus and returned into the reactor.

2. A process as claimed in claim 1, wherein the catalyst is a component of a mixture containing at least 60% by weight of formamide and said catalyst is returned from the apparatus into the reactor.

3. A process as claimed in claim 1, wherein said alcohol is methanol.

4. A process as claimed in claim 1, wherein carbon monoxide is supplied in the form of a mixture comprising carbon monoxide and hydrogen.

5. A process as claimed in claim 4, wherein the mixture comprising carbon monoxide and hydrogen is synthesis gas.

6. A process as claimed in claim 1, wherein unreacted carbon monoxide and/or unreacted ammonia and/or alcohol is separated off in the apparatus and recirculated to the reactor.

7. A process as claimed in claim 1, wherein the alcohol used is methanol and the molar ratio of ammonia to carbon monoxide to methanol in the reactor is 1.0:1.0–1.5:0.5–1.5.

8. A process as claimed in claim 1, wherein the concentration of the catalyst in the reactor is from 0.05 to 1.0 mol/l.

9. A process as claimed in claim 1, wherein the work-up in the apparatus is carried out by distillation.

10. A process as claimed in claim 1, wherein in the apparatus the alcohol(s) is (are) separated off in a first column and the catalyst is separated off in a second column from the reaction mixture containing formamide, ammonia, carbon monoxide, catalyst and at least one alcohol and returned into the reactor.

11. A process as claimed in claim 8, wherein the concentration of the catalyst in the reactor is from 0.2 to 0.25 mol/l.

* * * * *

UNITED STATES PATENT AND TRADEMARK OFFICE
CERTIFICATE OF CORRECTION

PATENT NO.    : 6,441,234 B1    Page 1 of 1
DATED         : August 27, 2002
INVENTOR(S)   : Dahlhaus et al.

It is certified that error appears in the above-identified patent and that said Letters Patent is hereby corrected as shown below:

<u>Title page,</u>
Item [73], should read:
-- [73] Assignee: BASF Aktiengesellschaft, Ludwigshafen, Germany (DE) --

Signed and Sealed this

Twenty-sixth Day of November, 2002

Attest:

Attesting Officer

JAMES E. ROGAN
*Director of the United States Patent and Trademark Office*